(12) United States Patent
Minas et al.

(10) Patent No.: US 11,944,489 B2
(45) Date of Patent: Apr. 2, 2024

(54) IMAGING ASSEMBLY FOR INTRAVASCULAR IMAGING DEVICE AND ASSOCIATED DEVICES, SYSTEMS, AND METHODS

(71) Applicant: PHILIPS IMAGE GUIDED THERAPY CORPORATION, San Diego, CA (US)

(72) Inventors: Maritess Minas, San Diego, CA (US); Princeton Saroha, Ladera Ranch, CA (US); Jeremy Stigall, Carlsbad, CA (US); David Kenneth Wrolstad, Fallbrook, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 17/963,265

(22) Filed: Oct. 11, 2022

(65) Prior Publication Data
US 2023/0038543 A1 Feb. 9, 2023

Related U.S. Application Data

(63) Continuation of application No. 16/088,141, filed as application No. PCT/IB2017/051681 on Mar. 23, 2017, now Pat. No. 11,464,480.

(60) Provisional application No. 62/315,395, filed on Mar. 30, 2016.

(51) Int. Cl.
*A61B 8/00* (2006.01)
*A61B 8/08* (2006.01)
*A61B 8/12* (2006.01)

(52) U.S. Cl.
CPC ............. *A61B 8/0891* (2013.01); *A61B 8/12* (2013.01); *A61B 8/445* (2013.01); *A61B 8/4488* (2013.01); *A61B 8/54* (2013.01)

(58) Field of Classification Search
CPC ......... A61B 8/0891; A61B 8/12; A61B 8/445; A61B 8/4488; A61B 8/54; A61B 8/0883
See application file for complete search history.

(56) References Cited

U.S. PATENT DOCUMENTS

| | | |
|---|---|---|
| 5,092,635 A | 3/1992 | Delange |
| 5,178,159 A | 1/1993 | Christian |
| 2002/0087083 A1 | 7/2002 | Nix |

(Continued)

FOREIGN PATENT DOCUMENTS

DE 9402697 U1 4/1994

*Primary Examiner* — Pascal M Bui Pho
*Assistant Examiner* — Alexei Bykhovski

(57) ABSTRACT

An intravascular imaging device is provided. In one embodiment, the intravascular imaging device includes a flexible elongate member sized and shaped for insertion into a vessel of a patient, the flexible elongate member having a proximal portion and a distal portion; a conductor extending between the proximal and distal portions of the flexible elongate member; an imaging assembly disposed at the distal portion of the flexible elongate member, the imaging assembly including: a flex circuit including a body and a tab extending therefrom, the tab having a conductive portion coupled to the conductor; and a support member around which the flex circuit is disposed, the support member including a shelf on which tab is positioned.

12 Claims, 20 Drawing Sheets

(56) References Cited

U.S. PATENT DOCUMENTS

| | | | |
|---|---|---|---|
| 2004/0044286 A1* | 3/2004 | Hossack | A61B 8/445 |
| | | | 600/585 |
| 2005/0261582 A1 | 11/2005 | Becker | |
| 2009/0030312 A1 | 1/2009 | Hadjicostis | |
| 2009/0318003 A1* | 12/2009 | Hossack | A61B 8/12 |
| | | | 439/299 |
| 2011/0166455 A1 | 7/2011 | Cully | |
| 2014/0005561 A1* | 1/2014 | Burkett | A61B 5/6876 |
| | | | 29/825 |
| 2014/0163664 A1 | 6/2014 | Goldsmith | |
| 2014/0187960 A1 | 7/2014 | Corl | |
| 2015/0305710 A1 | 10/2015 | Stigall | |
| 2016/0007962 A1* | 1/2016 | Esbeck | B06B 1/0215 |
| | | | 600/467 |

* cited by examiner

IMAGING ASSEMBLY FOR INTRAVASCULAR IMAGING DEVICE AND ASSOCIATED DEVICES, SYSTEMS, AND METHODS

CROSS-REFERENCE TO RELATED APPLICATIONS

This application is a continuation of U.S. patent application Ser. No. 16/088,141, filed Sep. 25, 2018, now U.S. Pat. No. 11,464,480, which is the U.S. National Phase application under 35 U.S.C. § 371 of International Application No. PCT/M2017/051681, filed on Mar. 23, 2017, which claims the benefit of Provisional Application Ser. No. 62/315,395, filed Mar. 30, 2016. These applications are hereby incorporated by reference herein.

TECHNICAL FIELD

The present disclosure relates generally to intravascular ultrasound (IVUS) imaging and, in particular, to the distal structure of an intravascular imaging device. For example, the distal structure can include a support structure and a flex circuit that are arranged to facilitate efficient assembly and operation of the intravascular imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse physiology within the human body is challenging. In that regard, components at the distal portion of the imaging device causes an area of high rigidity in the intravascular device, which increase the likelihood of kinking as the intravascular is steered through vasculature. When assembled, the distal components also have a large outer diameter, which makes navigation of small diameter blood vessels challenging.

Thus, there remains a need for intravascular ultrasound imaging system that overcomes the limitations of a rigid imaging assembly having a large diameter while achieving efficient assembly and operation.

SUMMARY

Embodiments of the present disclosure provide an improved intravascular ultrasound imaging system for generating images of a blood vessel. A distal portion of an intravascular imaging device can include a flex circuit and a support member around which the flex circuit is positioned. Electronic controllers and transducers, which are used to generate images of the vessel, are formed within the flex circuit. During assembly, the flex circuit can be rolled around the support member into a cylindrical shape. A proximal portion of the support member can include a shelf or a section of the support member body having a reduced diameter. A portion of the flex circuit at which electrical wires are soldered can rest on the shelf. The support member can also include a hole that defines a throughway that allows the electrical wires to extend between the flex circuit on an exterior of the intravascular device and an interior of the intravascular device. The shelf and throughway advantageously minimize the outer diameter of the intravascular device. A distal portion of the support member can be sized and shaped to increase the surface area of adhesive contact with a distal component, which allows for efficient assembly of the intravascular imaging device. A portion of the flex circuit can be wrapped in a spiral or helical configuration around the support member, which can contribute to increased flexibility of the imaging assembly.

In one embodiment, an intravascular imaging device is provided. The intravascular imaging device includes a flexible elongate member sized and shaped for insertion into a vessel of a patient, the flexible elongate member having a proximal portion and a distal portion; a conductor extending between the proximal and distal portions of the flexible elongate member; an imaging assembly disposed at the distal portion of the flexible elongate member, the imaging assembly including: a flex circuit including a body and a tab extending therefrom, the tab having a conductive portion coupled to the conductor; and a support member around which the flex circuit is disposed, the support member including a shelf on which tab is positioned.

In some embodiments, the shelf is sized and shaped to accommodate the tab. In some embodiments, the shelf comprises a portion of the support member having a reduced diameter. In some embodiments, the support member is substantially cylindrical and the shelf is planar. In some embodiments, the tab is disposed at a distal portion of the flex circuit and the shelf is positioned at a distal portion of the support member. In some embodiments, the support member defines a lumen, and wherein the support member includes a recess adjacent to the shelf, the recess defining throughway between the lumen and the tab through which the conductor extends.

In one embodiment, an intravascular imaging device is provided. The intravascular imaging device includes s flexible elongate member sized and shaped for insertion into a vessel of a patient, the flexible elongate member having a proximal portion and a distal portion; a conductor extending between the proximal and distal portions of the flexible elongate member; an imaging assembly disposed at the distal portion of the flexible elongate member, the imaging assembly including: a flex circuit coupled to the conductor; and a support member around which the flex circuit is disposed, the support member including: a lumen; and a recess defining throughway to the lumen through which the conductor extends.

In some embodiments, the recess is disposed at proximal portion of the support member. In some embodiments, the recess is shaped and shaped to accommodate the conductor. In some embodiments, the recess extends radially inward from an outer surface of the support member and through an inner surface of the lumen. In some embodiments, the flex circuit includes a body and a tab extending therefrom, the conductor being coupled to the flex circuit at a conductive portion of the tab; the support member includes shelf on which tab is positioned; and the recess is positioned adjacent to the shelf.

In one embodiment, an intravascular imaging device is provided. The intravascular imaging device includes a flexible elongate member sized and shaped for insertion into a vessel of a patient, the flexible elongate member having a proximal portion and a distal portion; an imaging assembly disposed at the distal portion of the flexible elongate member, the imaging assembly including: a flex circuit; and a support member around which the flex circuit is disposed, the support member having a flange at a distal portion thereof; a distal member extending from the support member and disposed around the flange, wherein the flange is sized and shaped to facilitate coupling between the distal member and the support member.

In some embodiments, the device further includes an adhesive disposed between the distal member and the support member, wherein the flange is sized and shaped to increase a coverage area of the adhesive between the distal member and the support member. In some embodiments, the flange is tapered. In some embodiments, the flange comprises a screw-thread pattern. In some embodiments, the screw thread pattern comprises a buttress thread pattern. In some embodiments, the flange is sized and shaped to facilitate locking engagement between the distal member and the support member.

In one embodiment, an intravascular imaging device is provided. The intravascular imaging device includes a flexible elongate member sized and shaped for insertion into a vessel of a patient, the flexible elongate member having a proximal portion and a distal portion; an imaging assembly disposed at the distal portion of the flexible elongate member, the imaging assembly including: a flex circuit; and a support member around which the flex circuit is disposed; wherein a portion of the flex circuit is wrapped in a spiral configuration around the support member.

In some embodiments, the flex circuit includes a first section having a plurality of transducers, a second section having a plurality of controllers, and a third section having a plurality of conductive traces facilitating communication between the plurality of the transducers and the plurality of controllers. In some embodiments, the third section is wrapped in a spiral configuration around the support member. In some embodiments, a value of a dimension of the flex circuit in the third section is less a value of the dimension of the flex circuit in the first and second sections. In some embodiments, a coating disposed over flex circuit, the coating configured to extend between gaps in the portion of the flex circuit is wrapped in a spiral configuration around the support member.

In one embodiment, a method of assembling an intravascular imaging device is provided. The method includes obtaining a flex circuit having a plurality of transducers, a plurality of controllers, and a plurality of conductive traces facilitating communication between the plurality of the transducers and the plurality of controllers; positioning the flex circuit around a support member, wherein the positioning includes wrapping a portion of the flex circuit around the support member in a spiral configuration; and coupling a flexible elongate member to at least one of the flex circuit or the support member such that the flex circuit and the support member are disposed at a distal portion of the flexible elongate member.

In some embodiments, the flex circuit includes a first section having the plurality of transducers, a second section having the plurality of controllers, and a third section having the plurality of conductive traces; and the third section is wrapped in the spiral configuration around the support member. In some embodiments, the method further includes applying a coating extending between gaps in the at least a portion of the flex circuit wrapped in a spiral configuration around the support member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
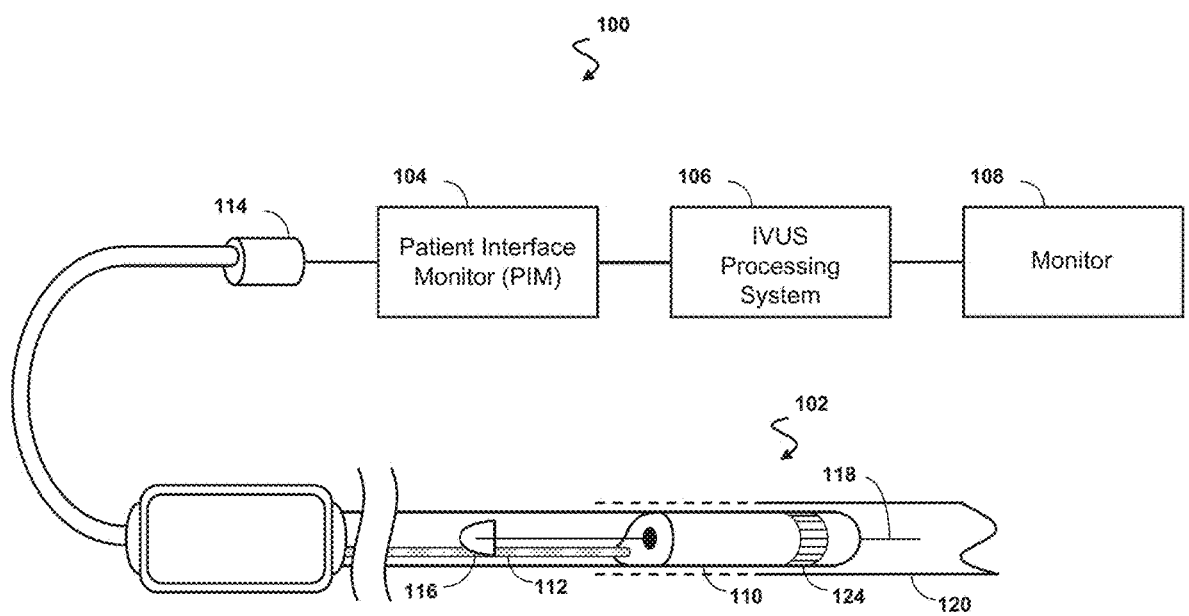
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
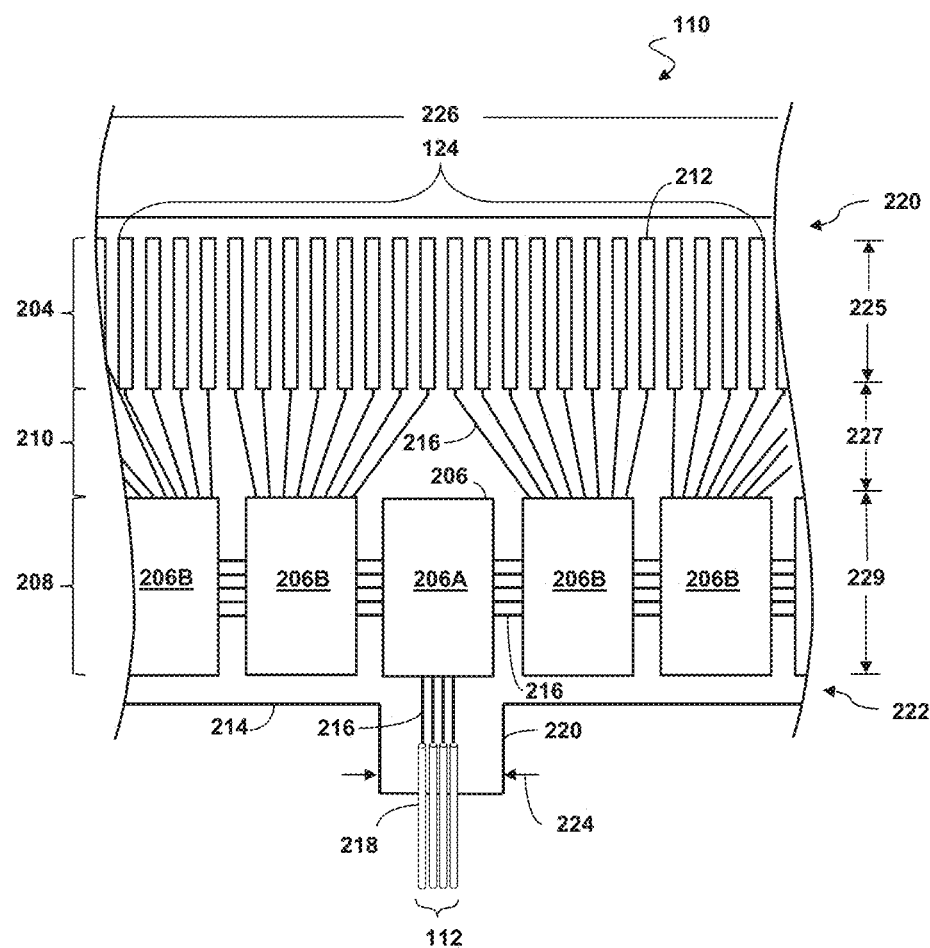
FIG. 2 is a diagrammatic top view of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

Figure 3:
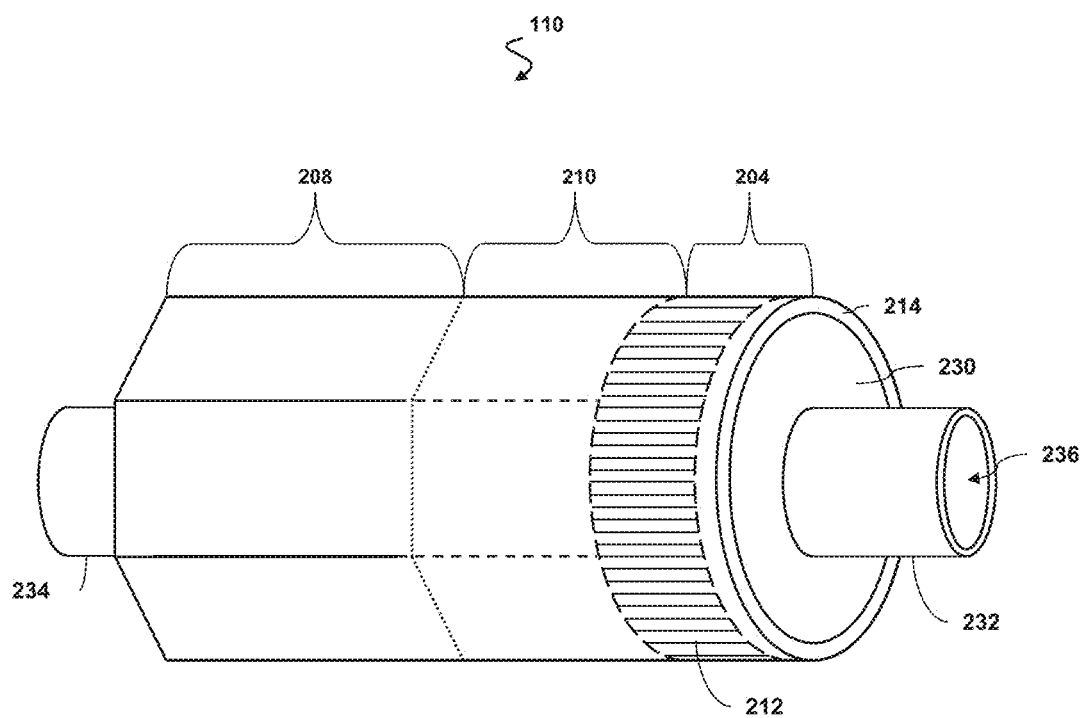
FIG. 3 is a diagrammatic side view of a scanner assembly in a rolled configuration around a support member, according to aspects of the present disclosure.

FIG. 2 is a top view of a portion of an ultrasound scanner assembly or imaging assembly 110 according to an embodiment of the present disclosure. The scanner assembly or imaging assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flex circuit 214 that is shown in a flat configuration in FIG. 2. FIG. 3 illustrates a rolled configuration of the flex circuit 214. The transducer array 202 is a non-limiting example of a medical sensor element and/or a medical sensor element array. The transducer control logic dies 206 is a non-limiting example of a control circuit. The transducer region 204 is disposed adjacent a distal portion 220 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the scanner assembly or imaging assembly 110 is described as including a flex circuit, it is understood that the transducers and/or controllers may be arranged to form the scanner assembly or imaging assembly 110 in other configurations, including those omitting a flex circuit.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 124 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON' (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 μm and 100 μm, with some particular embodiments being between 12.7 μm and 25.1 μm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 μm. For example, in an embodiment, 20 μm conductive traces 216 are separated by 20 μm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 114 are coupled to the flex circuit 214. For example, the bare conductors of the cable 114 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 220, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 220 and/or the conductor(s) 218 can be variously configured to facilitate efficient manufacturing and operation of the scanner assembly 110.

Figure 4:
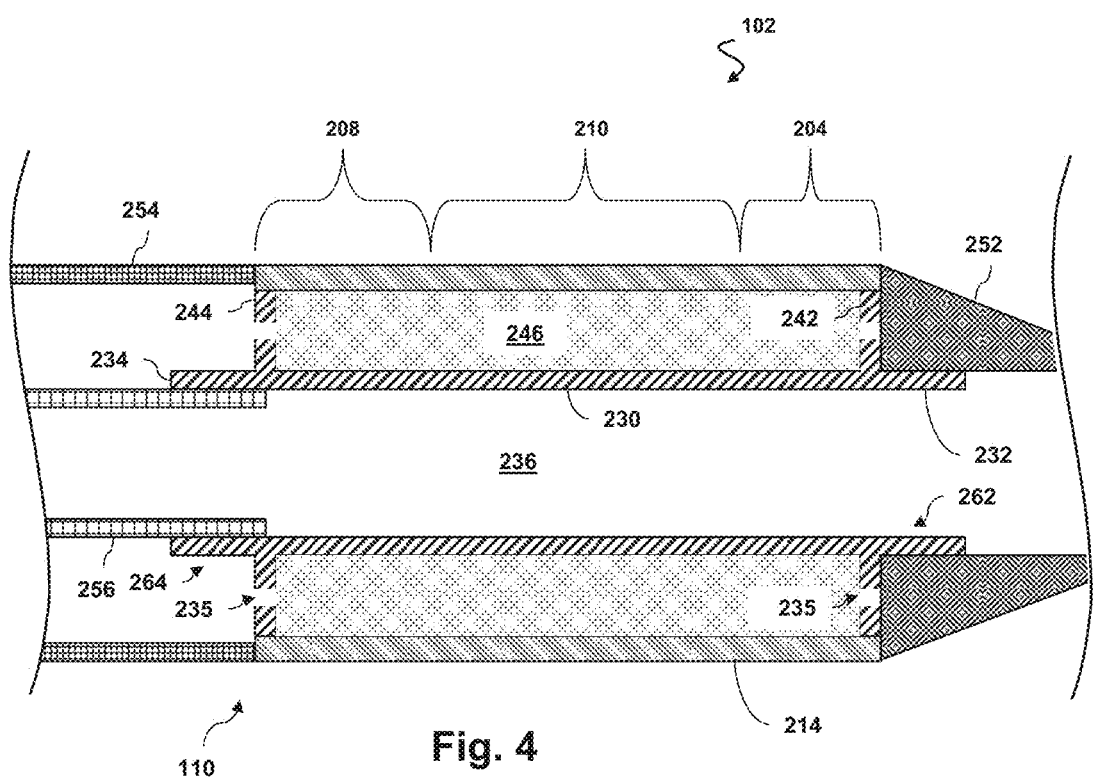
FIG. 4 is a diagrammatic cross-sectional side view of a distal portion of an intravascular device, according to aspects of the present disclosure.

In some instances, the scanner assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view with the flex circuit 214 in the rolled configuration around the support member 230, according to aspects of the present disclosure. FIG. 4 is a diagrammatic cross-sectional side view of a distal portion of the intravascular device 110, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another.

Stands 242, 244 that extend vertically are provided at the distal and proximal portions 262, 264, respectively, of the support member 230. The stands 242, 244 elevate and support the distal and proximal portions of the flex circuit 214. In that regard, portions of the flex circuit 214, such as the transducer portion 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244. To improve acoustic performance, any cavities between the flex circuit 214 and the surface of the support member 230 are filled with a backing material 246. The liquid backing material 246 can be introduced between the flex circuit 214 and the support member 230 via passageways 235 in the stands 242, 244. In some embodiments, suction can be applied via the passageways 235 of one of the stands 242, 244, while the liquid backing material 246 is fed between the flex circuit 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be flexible elongate member that extend from proximal portion of the intravascular device 102, such as the proximal connector 114, to the imaging assembly 110. For example, the proximal inner member 256 can be received within a proximal flange 234. The proximal outer member 254 abuts and is in contact with the flex circuit 214. A distal member 252 is coupled to the distal portion 262 of the support member 230. The distal member 252 can be a flexible component that defines a distal most portion of the intravascular device 102. For example, the distal member 252 is positioned around the distal flange 232. The distal member 252 can abut and be in contact with the flex circuit 214 and the stand 242. The distal member 252 can be the distal-most component of the intravascular device 102.

One or more adhesives can be disposed between various components at the distal portion of the intravascular device 102. For example, one or more of the flex circuit 214, the support member 230, the distal member 252, the proximal inner member 256, and/or the proximal outer member 254 can be coupled to one another via an adhesive.

Figure 5:
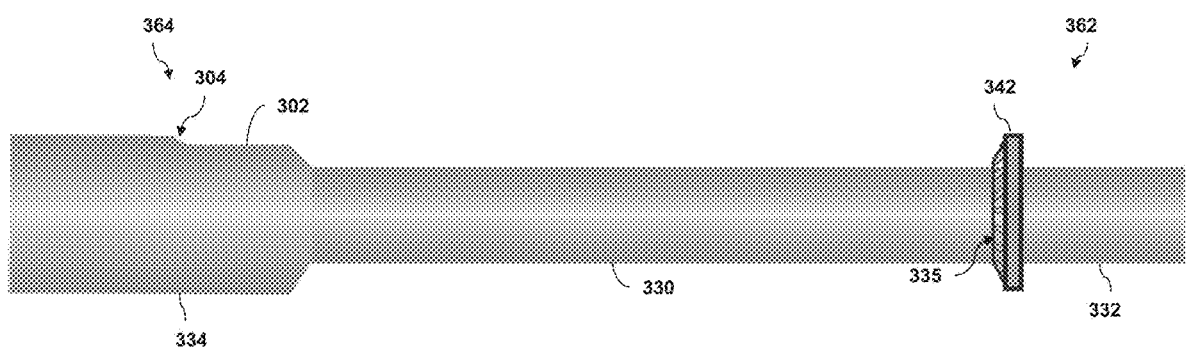
FIG. 5 is a diagrammatic side view of a support member, according to aspects of the present disclosure.
Figure 6:
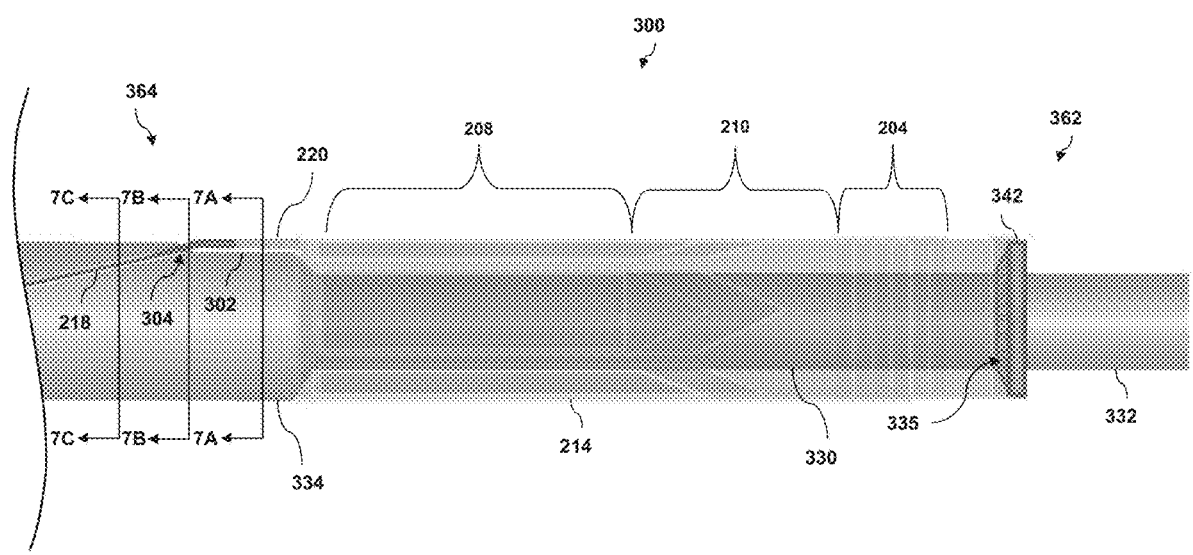
FIG. 6 is a diagrammatic side view of an imaging assembly, including a flex circuit in a rolled configuration around a support member, according to aspects of the present disclosure.
Figure 7A:
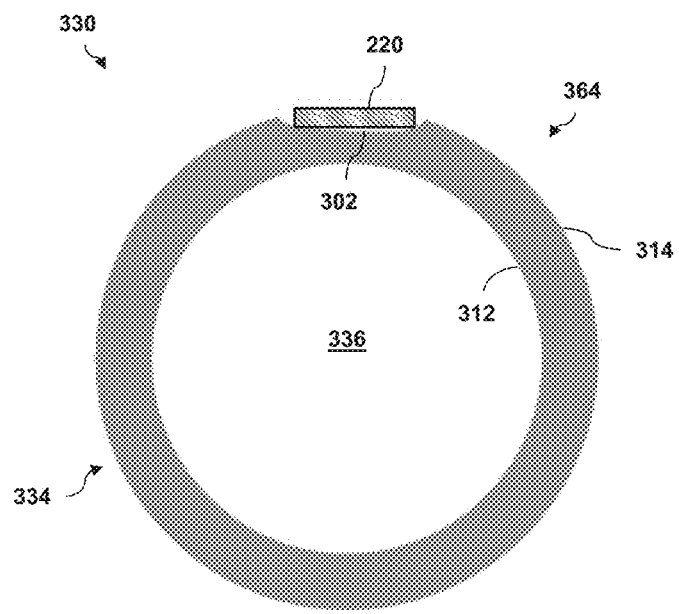
FIG. 7A is a diagrammatic cross-sectional front view of the imaging assembly of FIG. 6 along section line 7A-7A of FIG. 6, according to aspects of the present disclosure.
Figure 7B:
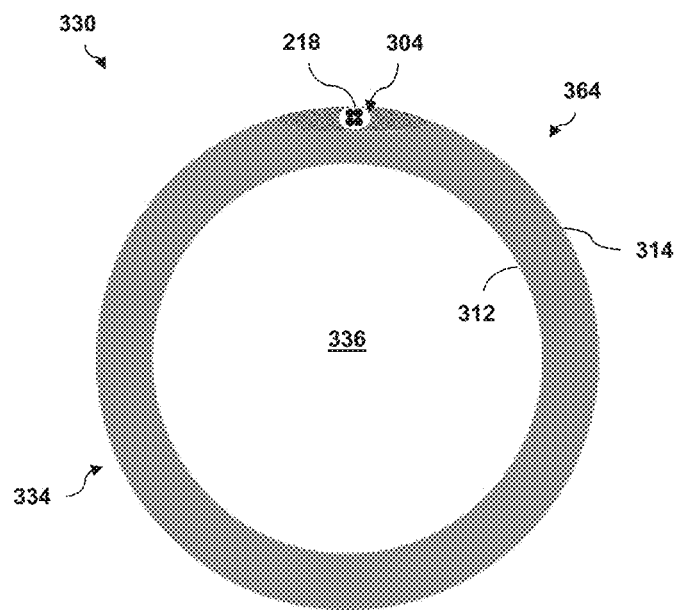
FIG. 7B is a diagrammatic cross-sectional front view of the imaging assembly of FIG. 6 along section line 7B-7B of FIG. 6, according to aspects of the present disclosure.
Figure 7C:
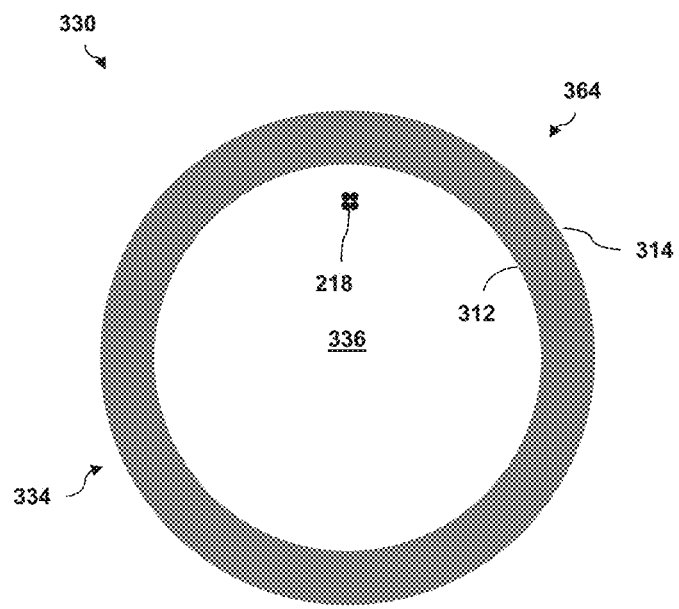
FIG. 7C is a diagrammatic cross-sectional front view of the imaging assembly of FIG. 6 along section line 7C-7C of FIG. 6, according to aspects of the present disclosure.

FIGS. 5, 6, 7A, 7B, and 7C illustrate an exemplary embodiment of a support member 330. FIG. 5 is a diagrammatic side view of the support member 330. FIG. 6 is a diagrammatic side view of an imaging assembly 300, including the flex circuit 214 in a rolled configuration around the support member 330. FIGS. 7A, 7B, and 7C are diagrammatic cross-sectional front views of imaging assembly 300 of FIG. 6 along section lines 7A-7A, 7B-7B, and 7C-C of FIG. 6, according to aspects of the present disclosure.

The support member 330 can be similar to the support member 230 in some aspects. The support member 330 includes a distal portion 362 and a proximal portion 364. A distal flange 332 and a stand 342 having passageways 335 are provided at the distal portion 362. The proximal portion 364 of the support member 330 is sized and shaped to accommodate components of the imaging assembly 300, including the conductors 218 and the conductor interface 220 flex circuit 214, and to allow efficient assembly the intravascular device.

A shelf 302 is provided on a proximal flange 334 of the support member 330. The shelf 302 is sized and shaped to accommodate the conductor interface 220. As shown in FIGS. 6 and 7A, when the flex circuit 214 is in a rolled configuration around the support member 330, the conductor interface 220 is received and rests on the shelf 302. The shelf 302 is an area of the proximal flange 334 having a reduced outer diameter relative to other parts of the proximal flange 334. The reduced outer diameter of the shelf 302 advantageously accommodates the thickness of conductor interface 220 and/or the conductors 218 so that the outer diameter of the imaging assembly 300 does not increase in the area of the conductor interface 220 when the flex circuit 214 is wrapped around support member 330. This advantageously prevents a bulge in the outer diameter of the imaging assembly 300 in the area of the conductor interface. The shelf can have a substantially planar surface that abuts or is in contact with an inferior side of the conductor interface 220. The conductor interface 220 can be affixed to the shelf 302 via an adhesive. In some embodiments, at least a portion of the shelf 302 is curved, such as in a concave manner, to provide space for the adhesive.

As shown in FIGS. 6 and 7B, the support member 330 can include a throughway 304. The throughway 304 can be a recess formed the support member 330 that defines a lumen. The conductors 218 extend from the conductor interface 220 into a lumen 336 of the support member 330 via the throughway or recess 304. The throughway 304 can be disposed at the proximal portion 364 of the support member 330. For example, the throughway 304 can be positioned adjacent to the shelf 302 such that the throughway 304 is proximate to the conductor interface 220 when the flex circuit 214 is wrapped around the support member 330. The recess 304 can be sized and shaped to accommodate the one, two, three, four or more conductors 218. For example, the diameter of the recess 304 can be selected to allow the one or more conductors 218 to pass between the outside of the support member 330 and the lumen 336. The recess 304 can extend radially inward from an outer surface 314 of the support member 330 and through an inner surface 312 of the lumen 336. FIG. 7C illustrates the one or more conductors 336 extending within the lumen 336. The throughway 304 advantageously minimizes the assembled, outer diameter of the imaging assembly 300 by guiding the conductors into the lumen 336 rather than the conductors 218 extending along the outer surface 314 of the support member 330. An intravascular device with the smaller diameter imaging assembly 300 can traverse physiology within the human body, such as a blood vessel, more efficiently than an intravascular device or imaging assembly with a larger diameter.

Figure 8A:
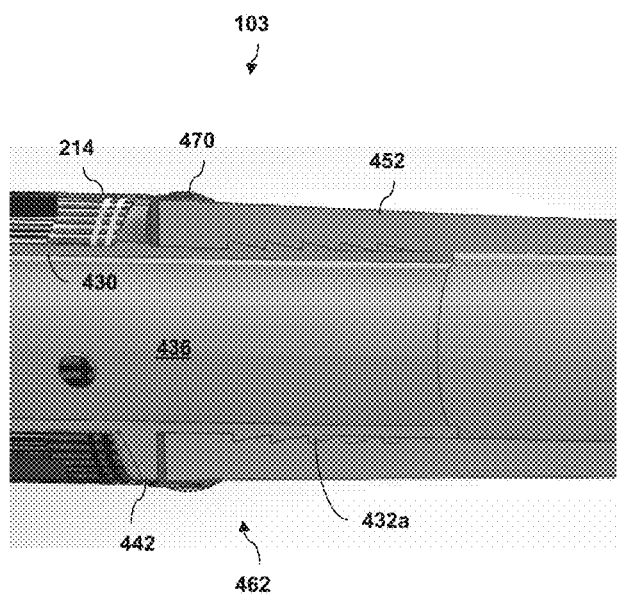
FIG. 8A is a diagrammatic cross-sectional side view of a distal portion of an intravascular device, including a distal portion of a support member, according to aspects of the present disclosure.
Figure 8B:
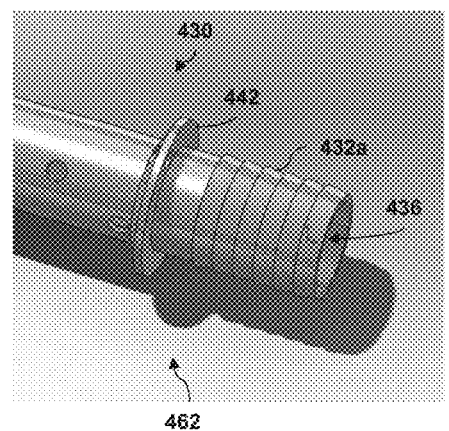
FIG. 8B is a diagrammatic perspective view of a distal portion of a support member, according to aspects of the present disclosure.

FIGS. 8A, 8B, 9, 10, 11, and 12 illustrate exemplary embodiments of a distal flange 432 of a support member 430. FIG. 8A is a diagrammatic cross-sectional side view of a distal portion of an intravascular device 103, including a distal portion 462 of a support member 430. FIG. 8B is a diagrammatic perspective view of the distal portion 462 of the support member 430. FIGS. 9, 10, 11, and 12 are diagrammatic cross-sectional side views of the distal portion 462 of the support member 430.

The support member 430 can be similar in some aspects to the support members 230 and 330. The support member 430 includes a stand 442 having an increased outer diameter relative to a central portion of the support member 430 (e.g., a portion of the support member 430 between proximal and distal stands, or between the stand 442 and an increased diameter proximal portion of the support member 430). The stand 442 is configured maintain a space between the flex circuit 214 and the central portion of the support member 430 to facilitate operation of the transducers of the flex circuit 214. The support member 430 defines a lumen 436 sized and shaped to receive a guide wire.

To assemble the intravascular device 103, adhesive 470 can be positioned on the distal flange 432 and then the distal member 452 is positioned around the distal flange 432 to the couple to the distal member 452 and the support member 430. The shape of the distal flange 432 can determine the surface area of contact between the distal member 452 and the distal flange 432. An increased surface area of contact allows for additional adhesive to bind the distal member 452 and the distal flange 432 together. Various shapes of the distal flange 432, such as those illustrated in FIGS. 8A-12, can facilitate efficient coupling between the distal member 452 and the distal flange 432. The shapes of the distal flange 432 can be manufactured according to any suitable process. For example, the distal flange 432, as well as support member 430, can be machined, laser cut, molded, and/or combinations thereof.

Figure 9:
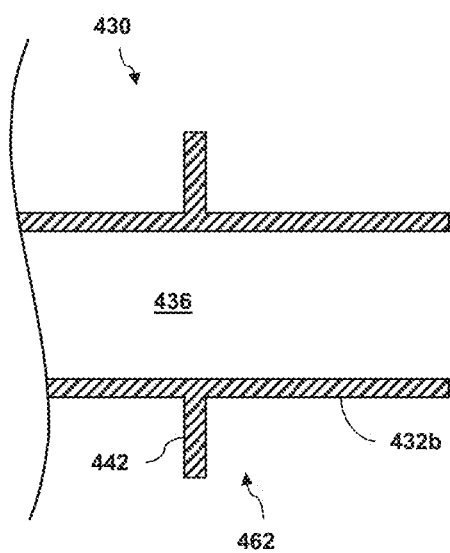
FIG. 9 is a diagrammatic cross-sectional side view of a distal portion of a support member, according to aspects of the present disclosure.
Figure 10:
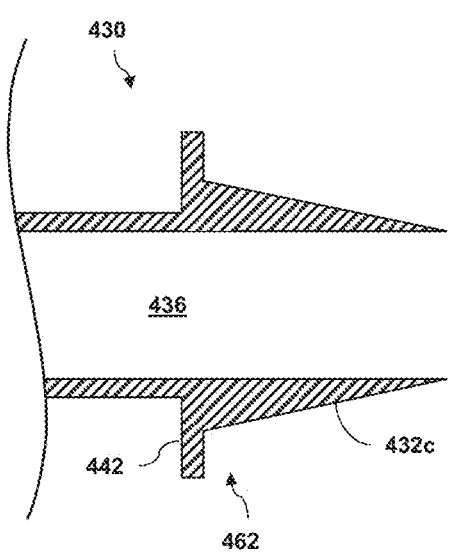
FIG. 10 is a diagrammatic cross-sectional side view of a distal portion of a support member, according to aspects of the present disclosure.
Figure 11:
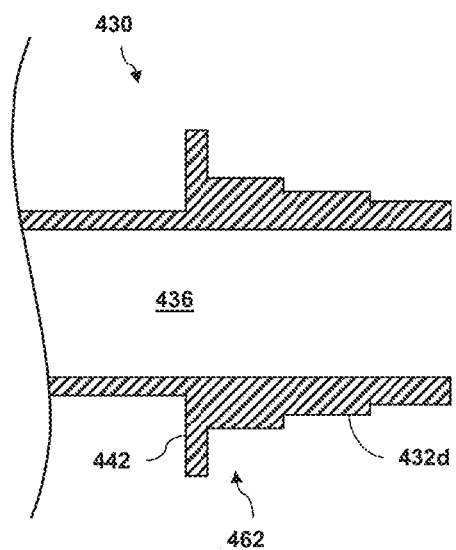
FIG. 11 is a diagrammatic cross-sectional side view of a distal portion of a support member, according to aspects of the present disclosure.
Figure 12:
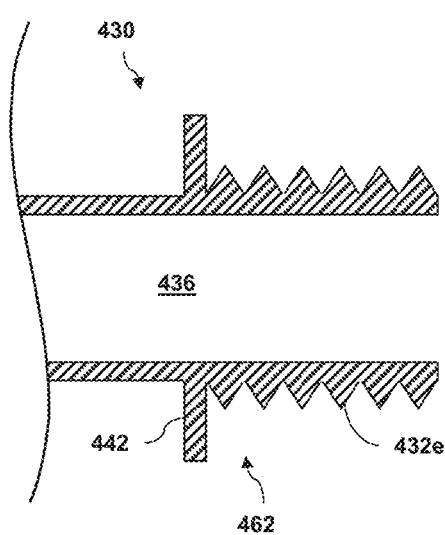
FIG. 12 is a diagrammatic cross-sectional side view of a distal portion of a support member, according to aspects of the present disclosure.

FIGS. 8A and 8b show a distal flange 432a having a screw thread pattern, such as a buttress thread pattern. FIG. 9 illustrates the distal portion 462 of the support member 430 having a straight or linear cross-sectional profile such that a distal flange 432b is substantially cylindrical. A distal flange 432c of FIG. 10 has a tapered cross-sectional profile. FIG. 11 shows the distal flange 432d having a stair step pattern. A distal flange 432e of the FIG. 12 has a screw thread pattern. As similarly described above, the various shapes of the distal flange 432 advantageously provide additional coverage area for adhesive to be positioned between the distal member 452 and the distal flange 432. One or more of the shapes of the distal flange 432, such as the screw thread pattern of distal flange 432e (FIG. 12) and/or the buttress thread pattern of distal flange 432a (FIGS. 8A and 8B) can also provide locking engagement of the distal member 452 and the distal flange 432a after the distal member 452 is slid over and around the distal flange 432a. In that regard, the crests of the distal flanges 432a, 432e can engage the flexible body of the distal member 452 such that removal of the distal member 452 is inhibited after the distal member 452 is slid over and around the distal flange 432a. The roots of the distal flanges 432a, 432e can provide additional areas for the adhesive to reside and to facilitate adhesion of the distal member 452 and the support member 430.

Figure 13:
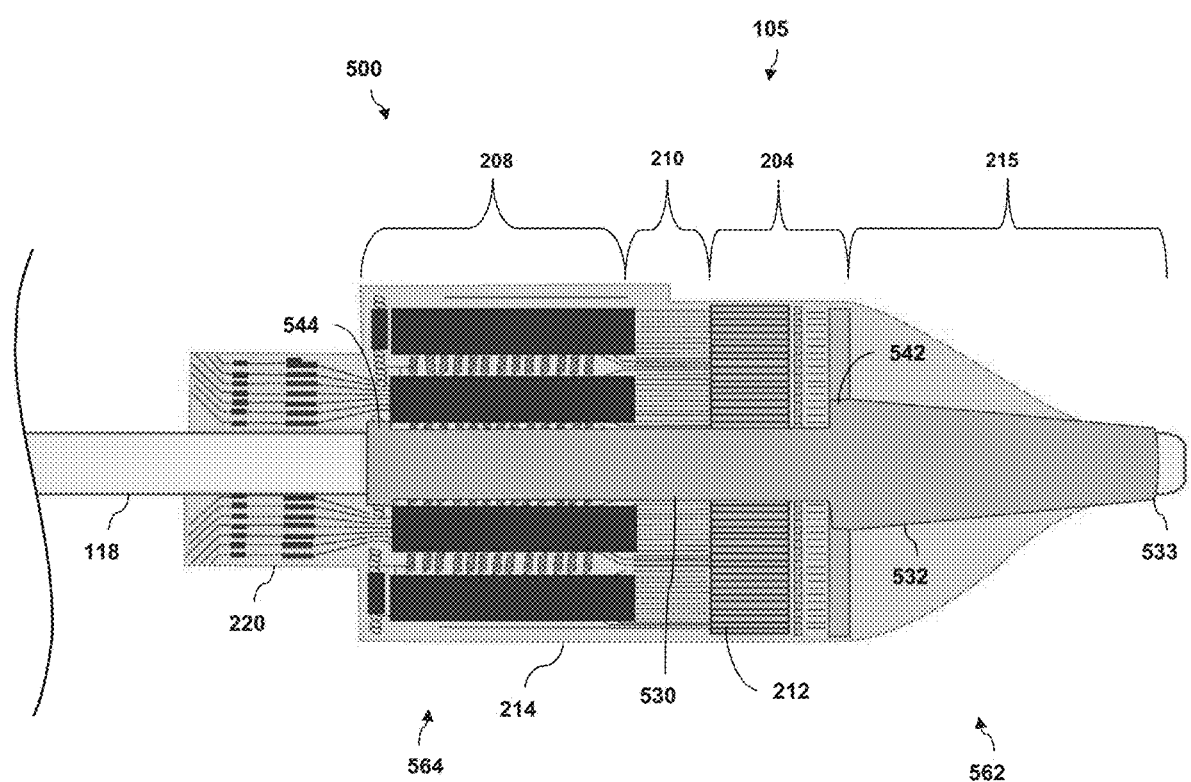
FIG. 13 is a diagrammatic top view of a distal portion of an intravascular device, including a distal portion of a support member, according to aspects of the present disclosure.

FIG. 13 is a diagrammatic top view of a distal portion of an intravascular device 105, including a distal portion 562 of a support member 530. Support member 530 can be similar to the support members 230, 330, and 430 in some aspects. The intravascular device 105 includes an imaging assembly 500, such as the flex circuit 214. The flex circuit 214 is shown in a flat configuration, aligned with the support member 530, and prior to being wrapped around the support 530. Increased diameter portions 542, 544 support and elevate the flex circuit from a central body portion of the support member 530 that extends between the increase diameter portions 542, 544. While the illustrated embodiment shows that the increased diameter portion 544 has larger outer diameter than the increased diameter portion 542, it is understood that the increased diameter portions 542, 544 can have the same diameter, or the increased diameter portion 542 can have a smaller outer diameter than the increased diameter portion 544. The guide wire 118 extends through the lumen of the support member 530.

A distal flange 532 of the support member 530 defines a distal most-end 533 of the intravascular device 105. In that regard, the intravascular device 105 omits a distal member that would otherwise be the distal-most component of the intravascular device 105. By omitting a distinct distal member, the total number of components can be minimized, allowing for more efficient assembly of the intravascular device 105. The distal flange 532 is can have any shape, including the tapered shape shown in the illustrated embodiment. The flex circuit 214 can include a distal region 215 that extends distally of the transducer region 204. The distal region 215 is wrapped around the distal flange 532 to assemble the intravascular device 105. An adhesive can affix the inferior side of the distal region 215 to the outer surface of the distal flange 532.

Figure 14:
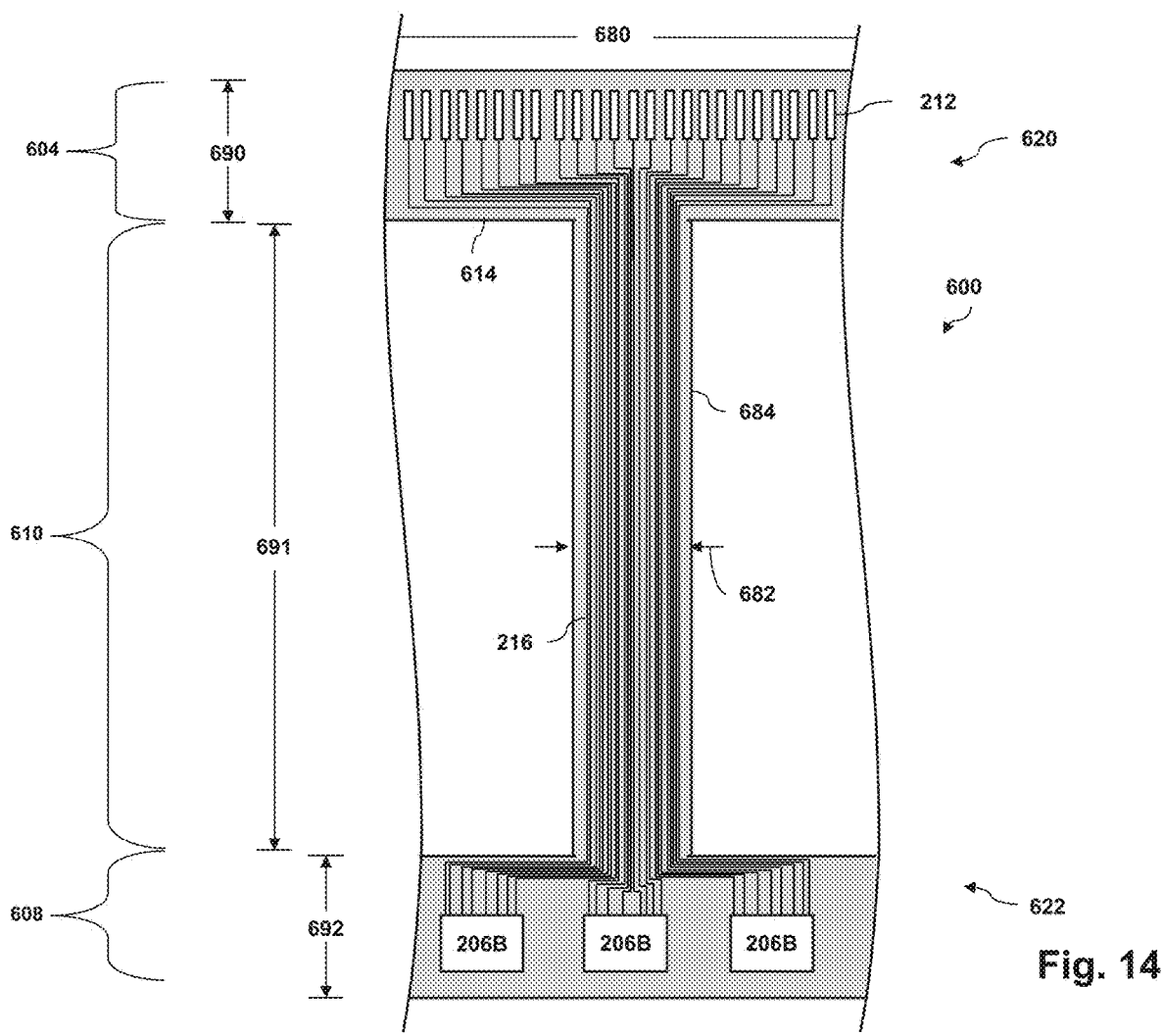
FIG. 14 is a diagrammatic top view of a scanner assembly in a flat configuration, according to aspects of the present disclosure.
Figure 15:
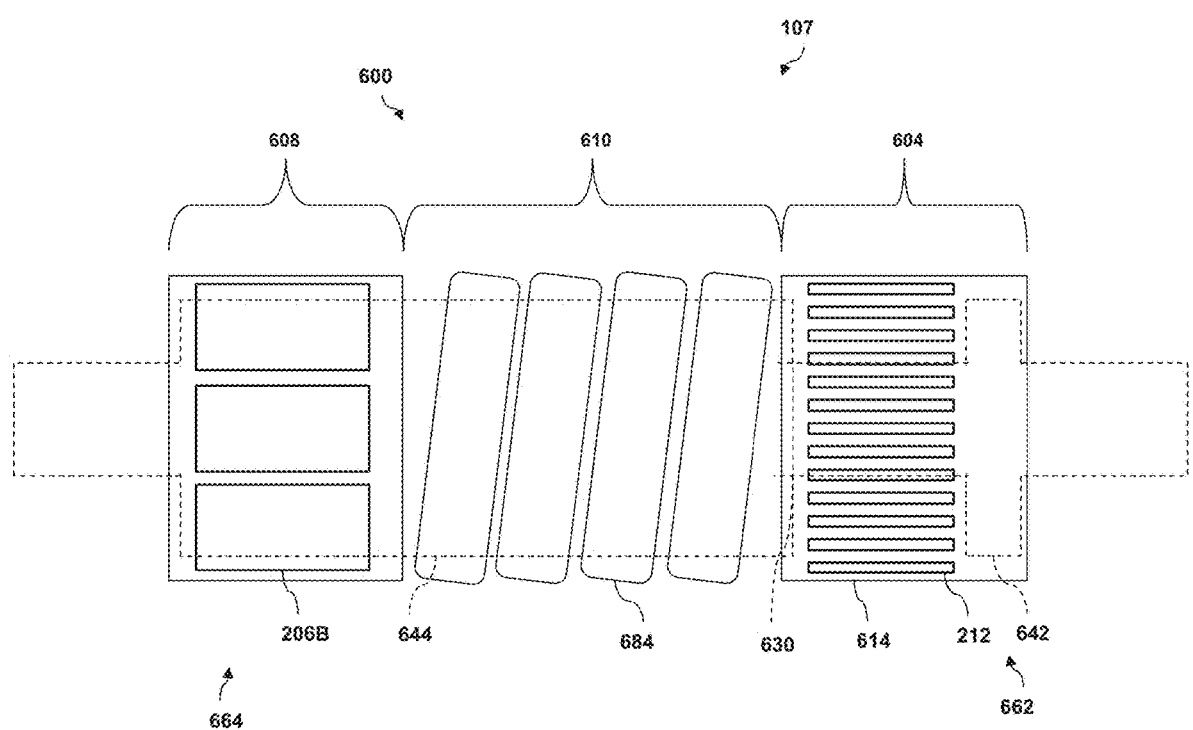
FIG. 15 is a diagrammatic side view of a scanner assembly in a rolled configuration around a support member, according to aspects of the present disclosure.
Figure 16:
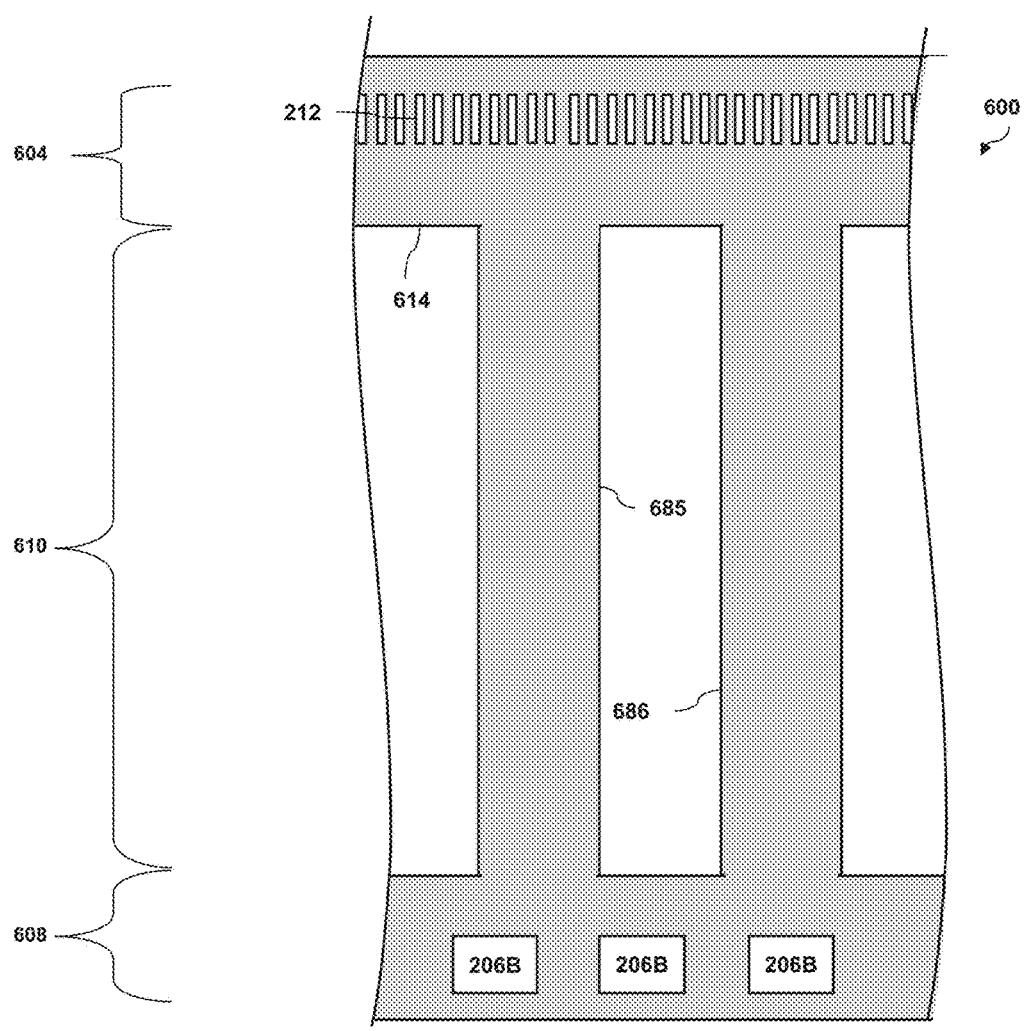
FIG. 16 is a diagrammatic top view of a scanner assembly in a flat configuration, according to aspects of the present disclosure.
Figure 17:
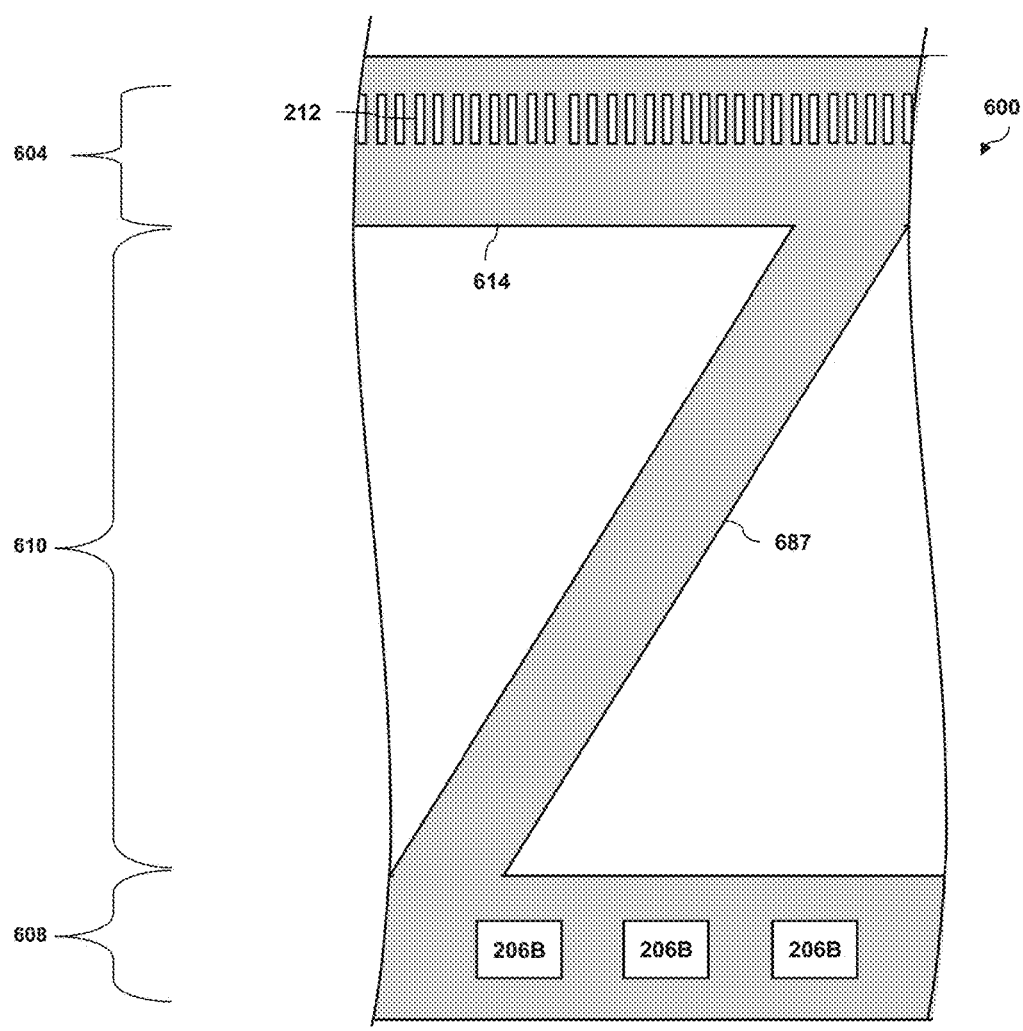
FIG. 17 is a diagrammatic top view of a scanner assembly in a flat configuration, according to aspects of the present disclosure.

FIGS. 14-17 illustrate exemplary embodiments of scanner assembly 600, including a flex circuit 614. A least a portion of the flex circuit 614 is configured to be spirally or helically wrapped around a support member 630. The scanner assembly 600 can be positioned at a distal portion of an intravascular device 107. Having a portion of the flex circuit 614 in a spiral or helical configuration can advantageously increase the flexibility of the scanner assembly 600 and decrease the likelihood of kinking while the intravascular device 107 is navigated through a patient's vasculature. FIGS. 14, 16, and 17 are diagrammatic top views of a scanner assembly 600 in a flat configuration. FIG. 15 is a diagrammatic side view of the scanner assembly 600, including the flex circuit 614, in a rolled configuration around the support member 630.

The scanner assembly 600 and the flex circuit 614 can be similar in some respects to scanner assembly 110 and the flex circuit 214, respectively. The imaging assembly 600 includes a transducer region 604 having a plurality of transducers 212 at a distal portion 620 and a controller region 608 having plurality of controllers 206B at a proximal portion 622. A transition region 610 having a plurality of conductive traces 216 extending in a central portion between the distal and proximal portions 620, 622 facilitates communication between the plurality of transducers 212 and a plurality of controllers 206B. The transition region 610 comprises a strip 684 on which the conductive traces 216 are formed. One dimension of the strip 684, such as a width 682, can have a smaller value than a corresponding dimension, such as a width 680, of the transducer region 604 and/or the controller region 608. The width 682 of the transition region 610 and/or the strip 684 can be any suitable value, including between approximately 0.010" and 0.415". The width 680 of the transducer region 604 and/or the controller region 608 can be between approximately 0.081" and 0.415", for example. The width 680 and/or width 682 can be suitable for an intravascular device 102 having a size between approximately 2 Fr and approximately 10 Fr, for example. Another dimension of the strip 684, such as a length 691, can have a larger value than a corresponding dimension, such as lengths 690, 692 of the transducer region 604 and the controller region 608, respectively. The length 691 of the transition region 610 and/or the strip 684 can be any suitable value, including between approximately 0.005" and 5.000". In that regard, the length 691 can be suitable for a relatively short bendable transition region 610 and/or a relatively longer transition region that may be rolled approximately ten revolutions around an approximately 10 Fr intravascular device 102, for example. The length 690 of the transducer region 604 can be between approximately 0.025" and 0.250", for example. The length 692 of the controller region 608 can be between approximately 0.025" and 0.250", for example.

Figure 18:
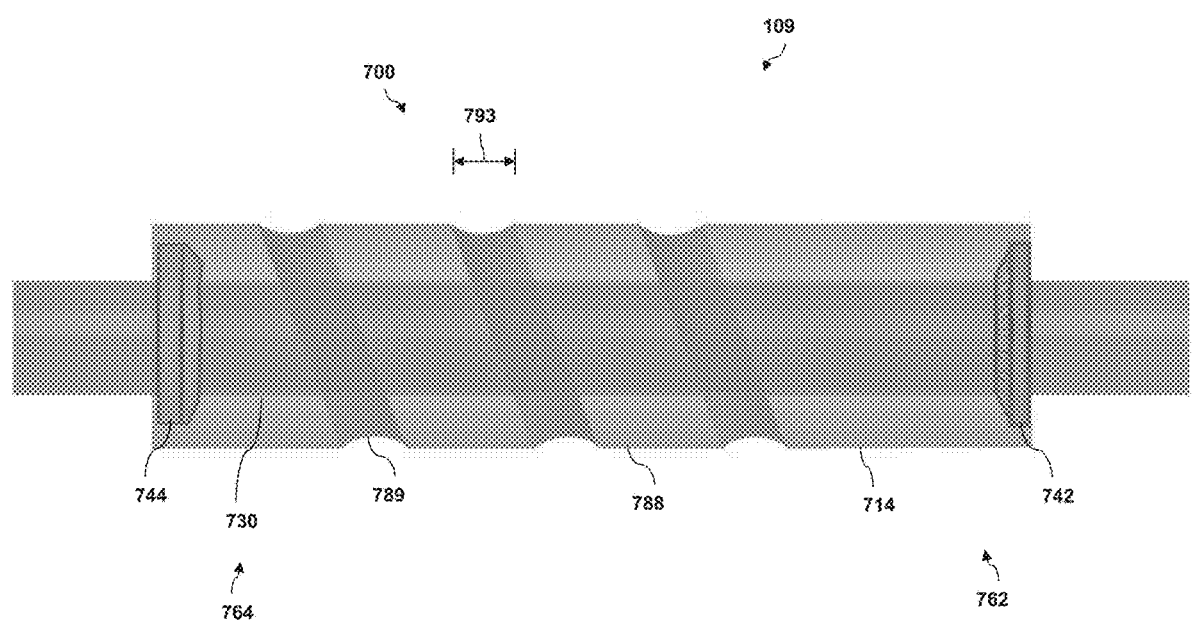
FIG. 18 is a diagrammatic side view of a scanner assembly in a rolled configuration around a support member, according to aspects of the present disclosure.

In the illustrated embodiment of FIG. 15, the flex circuit 614 is positioned around support member 630. Various regions of the flex circuit 614 can be positioned around the support member 630 in different configurations. For example, the transducer region 604 and the controller region 608 can have a cylindrical or cylindrical toroid configuration when rolled around the support member 630. The transition region 610 can have a spiral or helical configuration when positioned around the support member 630. The strip 684 of the transition region 610 is sized and shaped to be spirally wrapped around the support member 630. The strip 684 can be spirally wrapped around the support member 614 with any suitable number of windings, depending on the length 691. For example, the strip or spirally wrapped portion 684 can be wound around the support member one, two, three, four, or more times. The strip 684 can be wrapped with a right-handed or left-handed orientation in different embodiments (FIGS. 15 and 18).

The support member 630 can be variously sized and shaped to support the flexi circuit 614, including the strip or spirally wrapped portion 684. In FIG. 15, increased diameter portions 642, 644 support the flex circuit such that the transducers 212 are spaced from the body portion of the support member 630 extending between the increase diameter portions 642, 644. In that regard, the spirally wrapped portion 684 is in contact with the support member 630 as the spirally wrapped portion 684 is positioned around the increased diameter portion 684. In some embodiments, the spirally wrapped portion 684 is wrapped around a portion of the support member 630 having a relatively smaller diameter. In some embodiments, an acoustic backing material is disposed between in a space between the spirally wrapped portion 684 and the support member 630. For example, during assembly, the strip 684 can be wrapped around a mandrel that is later removed. The backing material can be introduced into the space between the flex circuit 614 and the support member 630.

While FIG. 14 illustrates that the transition region 610 of the flex circuit 614 includes one strip or spirally wrapped portion 684, it is understood that the transition region 610 can include any suitable number of strips, include one, two, three, four, or more strips. For example, FIG. 16 illustrates a configuration of the flex circuit including two strips 685, 686. The strips 685, 686 include conductive traces that facilitate communication between the transducers 212 and the controllers 206B. The multiple strips are sized and shaped to be helically or spirally wrapped around the support member 630.

The strip 684 (FIG. 14) and strips 685, 686 (FIG. 16) are positioned at right angles relative to the transducer region 604 and the controller region 608. Other suitable orientations of the one or more strips are contemplated. For example, as illustrated in FIG. 17, the strip 687 extends at an oblique angle relative to the transducer region 604 and the controller region 608. The strip 687 includes conductive traces that facilitate communication between the transducers 212 and the controllers 206B. The strip 687 is sized and shaped to be helically or spirally wrapped around the support member 630.

Yet other orientations for the transition region 610 are contemplated. For example, the one or more strips configured to be helically or spirally wrapped can be parallel or non-parallel. For example, the strips may intersect or overlap in some embodiments.

Figure 19:
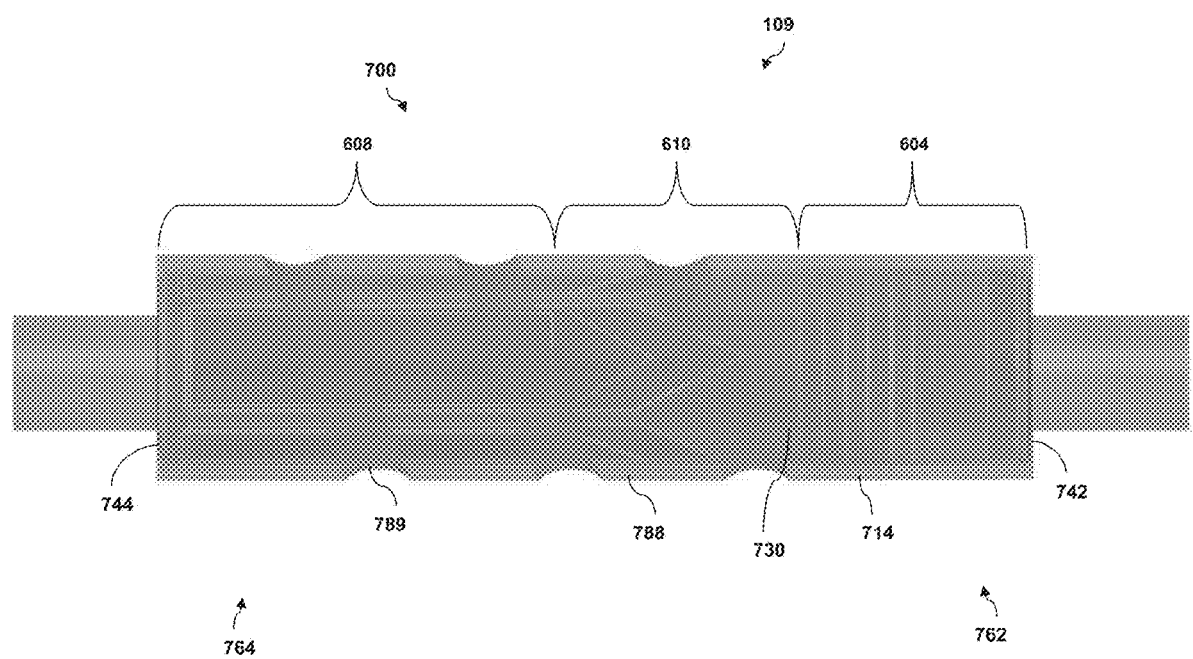
FIG. 19 is a diagrammatic side view of a scanner assembly in a rolled configuration around a support member, according to aspects of the present disclosure.

FIGS. 18 and 19 illustrate an exemplary embodiment the imaging assembly 700, including a flex circuit 714. A least a portion of the flex circuit 714 is configured to be spirally or helically wrapped around a support member 730. The scanner assembly 700 can be positioned at a distal portion of an intravascular device 109. FIGS. 18 and 19 are diagrammatic side views of the scanner assembly 700 in a rolled configuration. FIG. 19 illustrates exemplary positions of the various electronic components (e.g., controllers, transducers, and/or conductive traces) on the flex circuit 714, while FIG. 18 illustrates the flexible circuit 714 without the electronic components for clarity.

The flex circuit 714 is positioned around the support member 730. In that regard, the distal and proximal portions 762, 764 of the flex circuit 714 are supported by the stands 742, 744. The flex circuit 714 is spaced from the central portion of the support member 730 between the stands 742, 744. The space between the flex circuit 714 and the support member 730 can be filled with a backing material. A portion of the flex circuit 714, such as the strip 788 is spirally or helically wrapped around the support member 730. In some embodiments, the strip 788 is wrapped directly around the central portion of the support member 730 that has a smaller outer diameter than the stands 742, 744. In other embodiments, the strip 788 is spirally or helically wrapped around a mandrel surrounding the support member 730. An acoustic backing material is introduced between the support member 730 and the flex circuit 714, and the mandrel is removed after the backing material has cured such that the strip 788 is spirally or helically wrapped around the backing material.

A coating 789 has been applied to the imaging assembly 700. The coating 789 can be a flexible outer layer that seals the flex circuit 714. The coating 789 extends over the outer surface of the flex circuit 714. In particular, the coating 789 extends between the one or more gaps 793 between windings of the strip 788. In that regard, a dimension of the gaps 793, such as a width, can have any suitable value. For example, individual windings of the strip 788 can be closely-spaced such that the gaps 793 are relatively small or widely-spaced such that the gaps 793 are relatively large. The width of the gaps 793 can be between approximately 0.001" and approximately 0.040", in some embodiments. The width of the each of the gaps 793 can be equal or individual windings of the strip 788 can be spaced by different widths. The flex circuit 714 can have one or more gaps 793, depending on the number of windings of the strip 793 around the support member 730.

In the illustrated embodiment of FIG. 15, the spirally wrapped portion 684 of the flex circuit extends between the transducer region 604 and the controller region 608. In some embodiments, such as the embodiment of FIG. 19, the strip 788 can be helically or spirally wrapped around the support member 730 within the controller region 608 and the transition region 610. For example, the conductive traces formed within the spirally wrapped portion 788 can extend from a proximal portion of the one or more controllers within the controller region 608 to the one or more transducers within the transducer region 604.

Figure 20:
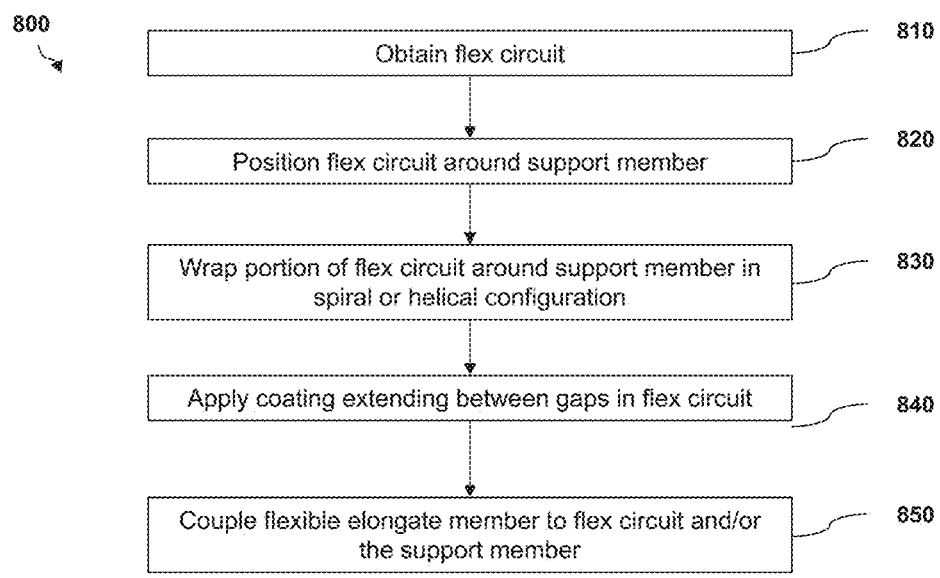
FIG. 20 is a flow diagram of a method of assembling an intravascular device, according to aspects of the present disclosure.

FIG. 20 is a flow diagram of a method 800 of assembling an intravascular imaging device, such as the intravascular devices 102, 105, 107, 109, as described herein. It is understood that the steps of method 800 may be performed in a different order than shown in FIG. 20, additional steps can be provided before, during, and after the steps, and/or some of the steps described can be replaced or eliminated in other embodiments. The steps of the method 800 can be carried out by a manufacturer of the intravascular imaging device.

At step 810, the method 800 includes obtaining a flex circuit. The flex circuit forms a part of an imaging assembly of the intravascular device. In that regard, the flex circuit comprises a plurality of transducers, a plurality of controllers, and a plurality of conductive traces facilitating communication between the transducers and the controllers. For example, the flex circuit can include a first section having the plurality of transducers, a second section having a plurality of controllers, and a third section having the plurality of conductive traces. In some embodiments, the first and second sections can be positioned at proximal and/or distal portions of the flex circuit. The third section having the conductive traces can extend in a central portion of the flex circuit between the first and second sections.

At step 820, the method 800 includes positioning the flex circuit around a support member. The support member can be a substantially cylindrical component. The flex circuit can be obtained in step 810 in a flat configuration. Step 820 can include transitioning at least a portion of the flex circuit into a rolled configuration around the support member. For example, the step 820 can include positioning the first, section, and/or third sections of the flex circuit around the support member. The step 820 can also include aligning the flex circuit with the support member. For example, the support member can include one more increased diameter portions to support the proximal and distal portions of the flex circuit. The proximal and/or distal portions of the flex circuit can be aligned with the support member prior to be rolled around the support member.

At step 830, the method 800 includes wrapping a portion of the flex circuit around the support member in a spiral or helical configuration around the support member. For example, the step 830 can include wrapping the third section having the plurality of conductive traces in a helical or spiral configuration around the support member.

In some embodiments, the steps 820 and 830 can include first rolling one of the proximal or distal portions of the flex circuit (e.g., the first or second section) into a cylindrical or cylindrical toroid configuration around the support member. Then, a central portion of the flex circuit (e.g., the third section) can be spirally or helically wrapped around the support member. Next, the other of proximal or distal portions of the flex circuit (e.g., the first or second section) can be rolled into a cylindrical or cylindrical toroid configuration around the support member.

In some embodiments, the method 800 includes disposing the conductive traces facilitating electrical communication between the transducers and controllers onto a film layer of a flexible polyimide material, such as KAPTON' (trademark of DuPont), forming the flex circuit. For example, the conductive traces can be wrapped in a spiral or helical configuration onto the flexible substrate. The pre-assembled flex circuit, including the transducers, controllers, and conductive traces, can then be wrapped/rolled around the support member to form the imaging assembly.

In some embodiments, the method 800 can include positioning a mandrel around the support member and positioning the flex circuit around the mandrel. The method 800 can also include introducing a liquid acoustic backing material between the flex circuit and the support member. The method 800 can also include removing the mandrel after the liquid acoustic backing material has cured.

At step 840, the method 800 can include applying a coating to the flex circuit. The coating can extend between gaps in the flex circuit, such as gaps in the windings in the portion of the flex circuit helically or spirally wound around the support member.

At step 850, the method 800 can include coupling the flex circuit and/or the support member to one or more flex elongate member. For example, one or more proximal flexible elongate members (e.g., an inner member and/or an outer member) are coupled to the flex circuit and/or the support member. In that regard, the flex circuit and/or the support member are positioned at the distal portion of the flexible elongate member. The method 800 can also include coupling the flex circuit and/or the support member to a distal component that defines a distal-most end of the intravascular imaging device. The method 800 can include introducing adhesive to affix the flex circuit and the support member and/or other components of the intravascular imaging device.

Various embodiments of an intravascular device and/or imaging assembly can include features described in U.S. Provisional App. No. 62/315,406, filed on Mar. 30, 2016, U.S. Provisional App. No. 62/315,421, filed on Mar. 30, 2016, U.S. Provisional App. No. 62/315,428, filed on Mar. 30, 2016, and U.S. Provisional App. No. 62/315,416, filed on Mar. 30, 2016, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device comprising:
a flexible elongate member sized and shaped for insertion into a vessel of a patient, wherein the flexible elongate member comprises a proximal portion and a distal portion;
a conductor extending between the proximal portion and the distal portion of the flexible elongate member; and
an imaging assembly disposed at the distal portion of the flexible elongate member, wherein the imaging assembly comprises:
a flex circuit comprising a body and a conductor interface extending from the body, wherein the conductor interface comprises a conductive portion coupled to the conductor; and
a support member, wherein the flex circuit is disposed around the support member such that the support member is distinct from the body and the conductor interface,
wherein the support member comprises a plurality of outer diameters along a length of the support member,
wherein the plurality of outer diameters comprises a first diameter and a second diameter,
wherein the first diameter is greater than the second diameter, and
wherein the second diameter comprises a shelf on which the conductor interface is positioned.

2. The intravascular imaging device of claim 1, wherein the shelf is sized and shaped to accommodate the conductor interface such than an outer diameter of the imaging assembly does not increase in an area comprising the shelf and the conductor interface.

3. The intravascular imaging device of claim 1, wherein the support member is cylindrical and the shelf is planar.

4. The intravascular imaging device of claim 1, wherein the conductor interface is disposed at a distal portion of the flex circuit and the shelf is positioned at a proximal portion of the support member.

5. The intravascular imaging device of claim 1, wherein the first diameter is proximal of the second diameter.

6. The intravascular imaging device of claim 1,
wherein the plurality of outer diameters further comprises a third diameter, a fourth diameter, and a fifth diameter, and
wherein the support member comprises:
- a first segment comprising the first diameter;
- a second segment comprising the second diameter, wherein the second segment is distal to the first segment;
- a third segment comprising the third diameter, wherein the third segment is distal to the second segment, wherein the third diameter is less than the second diameter;
- a fourth segment comprising the fourth diameter, wherein the fourth segment is distal to the third segment, wherein the fourth diameter is greater than the third diameter; and
- a fifth segment comprising the fifth diameter, wherein the fifth segment is distal to the fourth segment, wherein the fifth diameter is equal to the third diameter.

7. The intravascular imaging device of claim 1,
wherein the support member defines a lumen, and
wherein the support member comprises a recess defining throughway between the lumen and the conductor interface through which the conductor extends.

8. The intravascular imaging device of claim 7, wherein the recess is adjacent to the shelf.

9. The intravascular imaging device of claim 7, wherein the recess is disposed proximal of the shelf.

10. The intravascular imaging device of claim 7, wherein the recess is sized and shaped to accommodate the conductor such that an outer diameter of the imaging assembly does not increase in an area comprising the conductor and the recess.

11. The intravascular imaging device of claim 7, wherein the recess extends radially inward from an outer surface of the support member and through an inner surface of support member to the lumen.

12. The intravascular imaging device of claim 7, wherein the recess is positioned between the first diameter and the second diameter along the length of the support member.

* * * * *